United States Patent
Van Oosterom et al.

(10) Patent No.: US 11,439,399 B2
(45) Date of Patent: Sep. 13, 2022

(54) SURGICAL DEVICE FOR ENABLING ANASTOMOSIS AND A METHOD FOR COUPLING OF TISSUE PORTIONS INTRA-OPERATIVELY

(71) Applicants: Frederik Jan Theodoor Van Oosterom, Abcoude (NL); Alexander Petrus Jacobus Houdijk, Bergen (NL)

(72) Inventors: Frederik Jan Theodoor Van Oosterom, Abcoude (NL); Alexander Petrus Jacobus Houdijk, Bergen (NL)

( * ) Notice: Subject to any disclaimer, the term of this patent is extended or adjusted under 35 U.S.C. 154(b) by 0 days.

(21) Appl. No.: 17/285,257

(22) PCT Filed: Oct. 14, 2019

(86) PCT No.: PCT/NL2019/050678
§ 371 (c)(1),
(2) Date: Apr. 14, 2021

(87) PCT Pub. No.: WO2020/080937
PCT Pub. Date: Apr. 23, 2020

(65) Prior Publication Data
US 2021/0369280 A1    Dec. 2, 2021

(30) Foreign Application Priority Data
Oct. 15, 2018    (NL) .................................... 2021816

(51) Int. Cl.
*A61B 17/064*    (2006.01)
*A61B 17/115*    (2006.01)
(Continued)

(52) U.S. Cl.
CPC ....... *A61B 17/1155* (2013.01); *A61B 17/1114* (2013.01); *A61B 2017/00477* (2013.01)

(58) Field of Classification Search
CPC ......................... A61B 17/115; A61B 17/1155
See application file for complete search history.

(56) References Cited

U.S. PATENT DOCUMENTS 8,267,301 B2 *  9/2012  Milliman ............. A61B 17/068
                                                227/176.1
8,328,062 B2 * 12/2012  Viola .................. A61B 17/115
                                                227/181.1
(Continued)

FOREIGN PATENT DOCUMENTS

| CN | 200984210 Y | 12/2007 |
| CN | 202982106 U | 6/2013 |
| EP | 3000414 A1 | 3/2016 |

OTHER PUBLICATIONS

Chinese Office Action for corresponding Chinese Application No. 201980068172.3 dated Jun. 2, 2022 with English Translation.

*Primary Examiner* — Eyamindae C Jallow
(74) *Attorney, Agent, or Firm* — Browdy and Neimark, PLLC

(57) ABSTRACT

A surgical device for enabling gastrointestinal anastomosis using one or more tissue couplers, the device comprising a first working element and a second working element, the first working element being displace ably arranged with respect to the second working element so that at least a first relative stand and a second relative stand between the first working element and a second working element are provided, wherein in the first relative stand a coupling space is provided between the first working element and the second working element, for receiving a first tissue portion and a second tissue portion for coupling, wherein in the second stand the first working element cooperates with the second working element for depositing one or more couplers in the said coupling space, for achieving said coupling along a coupling region, wherein the first working element and/or (Continued)

the second working element comprise one or more first couplers and one or more second couplers, wherein the one or more first couplers define a tissue sealing line, wherein the second couplers define a respective virtual plane (P; P') that intersects the sealing line, and the second couplers spatially inter digitate with the first couplers, but do not overlap, with less compressive force on the tissues to be coupled in the healing line as compared to the compressive force on the tissues in the sealing line, defining a healing line in which circumstances are optimized for wound healing, and a sealing line that prevents bleeding and leakage of intestinal contents directly postoperatively.

13 Claims, 5 Drawing Sheets

(51) Int. Cl.
*A61B 17/11* (2006.01)
*A61B 17/00* (2006.01)

(56) References Cited

U.S. PATENT DOCUMENTS

| | | | |
|---|---|---|---|
| 2007/0175963 A1* | 8/2007 | Bilotti | A61B 17/115 227/179.1 |
| 2014/0074130 A1* | 3/2014 | Vestweber | A61B 17/1152 606/153 |
| 2014/0081176 A1 | 3/2014 | Hassan | |
| 2019/0328394 A1* | 10/2019 | Williams | A61B 17/064 |
| 2020/0337708 A1* | 10/2020 | Sgroi, Jr. | A61B 17/1155 |

\* cited by examiner

SURGICAL DEVICE FOR ENABLING ANASTOMOSIS AND A METHOD FOR COUPLING OF TISSUE PORTIONS INTRA-OPERATIVELY

FIELD OF THE INVENTION

The invention relates to a surgical device arranged for enabling surgical gastro-intestinal anastomosis, sealing and/or coupling.

The invention further relates to a method of coupling of tissue portions intra-operatively.

BACKGROUND OF THE INVENTION

In surgery, mechanical instruments may be used for replacing labor-intensive handwork, such as suturing of portions of tissues. Usually, the mechanical instruments provide a substantial improvement of the accuracy of surgical handling and have an additional advantage of being more reproducible and reliable than human handling.

In particular, in the field of intestinal surgery, the so-called staplers may be used in construction of anastomosis, i.e. a connection between two ends of intestine, for example when a part of a bowel has been resected. It will be appreciated that coupling of tissue portions may be carried out for any type of interventional handling. In addition, staplers are used to cut and seal stomach or intestines as part of salvage procedures where stomata are created and the stapled ends of intestines may be used for future re-anastomosis.

Currently, for connecting or cutting and sealing parts of an intestine a so-called stapling device is used. For instance in circular anastomotic stapling, two rows of staples are provided along substantially circular concentric rings having different diameter, wherein substantial spacing between staples forming each ring is provided. Staple orientation is circular or parallel along the concentric ring/the cutting edge of the intestine, and the lumen of the intestine. The staples are provided in an interspaced fashion—a staple of one concentric ring is arranged opposite to a spacing of the adjacent concentric ring (FIG. 1a). Anastomosis, coupling or cutting and sealing can also be performed using a linear stapling device where the conventional staple orientation is parallel to the knife that cuts both ends of the tissues to be connected (FIG. 1b). Linear staplers are often used to cut and seal ends of gastrointestinal tissues that are left inside the body for future anastomosis or to seal the end of the intestine that is used for side to end anastomosis.

However, anastomotic or coupling failure is reported with the use of conventional circular or linear stapling, as a result of jeopardized local perfusion at the anastomotic healing area, which may lead to necrosis of the comprised tissue resulting in leakage of the anastomosis. Also, leakage from the coupled region/tissues may also occur when the staples do not provide proper affixing of the tissue.

Secondly, the interspaced overlapping concentric staple/coupler lines in conventional stapling inhibit any concentric stretching of the anastomotic area, possibly adding to or leading to obstruction of passing of intestinal contents, also known as stricture or stenosis. On top of this, healing in ischemic circumstances induces an enhanced fibrotic reaction, leading to a thicker, more rigid anastomotic area/intestinal wall.

Finally, ischemia on the outer side or serosal side of the anastomotic area is an important inducing factor in the formation of adhesions of surrounding tissues to the anastomotic area.

Anastomotic leakage rate is (still) considerable. Anastomotic leakage leads to re-operation(s), significant morbidity and costs, and increased mortality. Also post-operative stricture and adhesion formation are frequently occurring complications, adding to post-operative morbidity of patients, jeopardising surgical results, and adding to medical costs.

Complication rates can be reduced by improving design of the stapler apparatus, hereby reducing morbidity, mortality and health care expenses.

SUMMARY OF THE INVENTION

It is an object of the invention to provide a surgical coupling device which enables reliable affixing of the tissue portions, while reducing complication rates. It is a further object of the invention to provide a surgical coupling device, wherein parts of a linear structure or a tubular structure, such as an intestine, may be reliably coupled.

To this end the surgical device for enabling gastro-intestinal anastomosis is characterized by the features of claim 1.

According to an aspect of the invention, a surgical device is used for enabling gastro-intestinal anastomosis using staples or tissue couplers, the device comprising a first working element and a second working element, the first working element being displaceably arranged with respect to the second working element so that at least a first relative stand and a second relative stand between the first working element and a second working element are provided, wherein in the first relative stand a coupling space is provided between the first working element and the second working element, for receiving a first tissue portion and a second tissue portion for coupling, wherein in the second stand the first working element is adapted to cooperate with the second working element for depositing staples or couplers in said coupling space, for achieving said coupling along a coupling region, wherein the first working element and/or the second working element comprise first staples or couplers and second staples or couplers, wherein the first staples or couplers are aligned parallel to the cut line of the tissues, i.e. a line along which the tissue is cut, to define a tissue sealing line, wherein the second staples or couplers each define a respective virtual plane (P; P') that intersects the tissue sealing line in an intersection point, wherein the virtual planes have an orientation that is normal with respect to an orientation of the said tissue sealing line in the intersection point, to define a tissue healing line, and wherein a first distance between two adjacent first staples or couplers is smaller than a second distance between two adjacent second staples or couplers, when projected onto the tissue sealing line, and wherein the second staples or couplers interdigitate and not overlap with the first staples or couplers.

For example, according to a non-limiting embodiment e.g. of a circular coupling process, the first working element and/or the second working element can comprise said plurality of staples or couplers, both in a circular orientation and in a radial orientation so that upon coupling a substantially circular sealing coupling occurs at an inner coupling region of e.g. tubular tissue portions, and the radial coupling geometry occurs at an outer coupling region of such tubular tissue portions.

For example, in a non limiting embodiment, one or more of staples or couplers (i.e. coupling means, coupling structures) can be staples.

For example, the tissue portions to be coupled to each other can be tubular tissue portions, e.g. two opposite ring-shaped tissue parts. It is found that substantial improvement of healing may be reached when in a first section of the coupling region a substantially circular connection is made using one or more first couplers (for example one or more first staples, e.g. an array of staples) which is/are oriented substantially along a circular line which is substantially concentric with and adjacent to a cut end of the tubular tissues, forming a sealing line (FIG. 2a). This same principle applies for a linear stapling device (FIG. 2b).

Pressure of compression of the tissues to be coupled in the first section or sealing line is high such that optimum sealing effect is established, preventing early leakage of intestinal fluids outside the tubular tissue, and ensuring hemostasis of the cut ends of the intestinal parts (FIG. 3a). Also this said compression pressure in the first section is high, resulting in local tissue necrosis after 4-6 hours and tissue loss after 3-5 days, shedding debris and the staples/couplers of the concentric staple line into the intestinal lumen.

Additionally, in an embodiment the surgical device is configured to provide one or more second couplers (e.g. one or more second staples, radial staples) in a second section of the coupling region or healing line, that is more remote from the cut end and distinct of the sealing line. Particularly, the device can be configured to provide one or more second staples, with a staple base in a substantially radial orientation or substantially perpendicular to a cut end of tubular tissues. This second section is the anastomotic healing line. Pressure of compression of the tissues to be coupled in this healing line is low and such that careful apposition of the tissues is obtained, with the least interference of local intestinal blood flow as possible (FIG. 3b, 4a).

The sealing line staples are nearly directly adjacent and the healing line staples are more widely apart, leaving more room for circulation in between the staples.

The staples of the healing line are positioned interdigitating with the staples of the sealing line, keeping maximally away from the high pressures zones inflicted by the sealing line.

The radial orientation allows distension of the tissue in the early postoperative phase of edema. Staples or couplers in the second section or healing zone can be designed with longer legs and/or less inward bending, leading to more space for the comprised tissue, as compared to staples or couplers in the first section (FIG. 3b, 4b). Regarding the afore-mentioned first section and second section of the coupling region, particularly, the first section (or sealing line) of the coupling region extends between the cut end/cut line and the second section (or healing line) of the coupling region. More details on this embodiment are discussed with reference to FIGS. 2a, 2b, 3a, 3b, 4.

The improvement in the coupling effect may be explained by the fact that the first, e.g. circular, sealing line, provided by the one or more first staples or couplers, serves for a good physical attachment of the cut ends of the tissues, such as intestine sections. The fact that the first couplers are oriented along the cut end maximizes the sealing effect which is applied to the cut ends of the tissues for keeping them together, ensuring both closure of the lumen and hemostasis of the cut blood vessels along the cut ends, preventing leakage of intestinal contents outside of the intestine and preventing excessive bleeding of the cut ends into the intestinal lumen respectively. The fact that compression force exceeds tissue perfusion pressure leads to necrosis of the inner ring of the anastomosis and shedding of this necrotic tissue will take place in the early phase of anastomotic healing. Integrity of the anastomosis following this period of wound healing is then provided by the second section of radial staples or couplers, which has formed a waterproof barrier by then. This loss of the concentric sealing staple/coupler line serves two purposes: the structural stricture that is formed by the concentric staple line is discarded and the ischemic stimulus for an overly fibrotic reaction is gone.

Secondly, the second staples or couplers allow better perfusion of the anastomotic region (healing zone) by not obstructing blood flow in longitudinally arranged blood vessels, especially in the early postoperative phase with edema (FIG. 4a/invention vs. 4b/conventional stapling). Hence there is less ischemic stimulus on the outside of the intestine aiding in prevention of adhesion formation. Also, the radial orientation of the staples or couplers in the second section and the wide interspaces inbetween staples or couplers form no structural mechanical obstruction to concentric stretching/distension of the anastomotic area after shedding of the inner ring (FIG. 5b/invention vs 5a/conventional stapling).

Finally, compression pressure in the staples or couplers in the second section or healing line is adjusted so as to ensure proper apposition of the intestinal parts and to interfere as least as possible with local tissue perfusion at the same time. In a still further embodiment of the device according to the invention, it further comprises a configuration or regulator for controlling pressure applied in use to the tissue for the second stand between the first working element and the second working element.

It is found that excessive pressure applied to the tissue by a coupler or staple may cause tissue damage, which is undesirable for purpose of anastomotic healing. In order to solve this problem the device according to the invention may comprise a suitable configuration or pressure meter and regulator for limiting the allowable applied pressure. It is found that it is advantageous to limit the pressure of the anastomotic healing line at a maximum value of about 25 mm Hg, tissue perfusion pressure. The one or more first staples or couplers are applied to the tissue at a larger pressure than that is used to apply the second coupler(s) to the tissue. Thus, the first coupler(s) can provide hemostasis and a proper sealing, preventing leakage of intestinal contents. The second coupler(s) can just hold the tissue parts together, with pressure permitting tissue perfusion, allowing primary healing, without substantially locally blocking e.g. blood flow (FIG. 4a).

In a further or other embodiment of the device according to the invention, the pressure difference between the first and second couplers or staples can be effectuated by a difference in height of the drivers, pushing the couplers or staples in the first working element downward, and/or a difference in height of anvil depth in the second working element, bending the legs of the staples. Combination of adjustments or single adjustment of either the driver height and the anvil depth leads to more space in the bended staple for the comprised tissue at the second section healing line as compared to the sealing line (of FIGS. 3a and 3b).

Also length of the legs of the staples or couples can differ between the staples/couplers of the first section or sealing line (shorter) (FIG. 3a) as compared to the legs of the staples/couplers of the second section or healing line (FIG. 3b), permitting more space in the bended staple for the comprised tissue in the healing line.

In an embodiment of the device better tissue perfusion is achieved by the substantially radial or perpendicular oriented second staples in comparison to the circular oriented first staples by longer length of the staple legs of the radial oriented second staples that bend simultaneously with the circular oriented staples but in a deeper gap in the anvil allowing a substantially lower compression of the tissue on release of the applied pressure by the device needed to bend the staple legs (such as for example shown in FIGS. 3a and 3b).

The orientation of the staplers as is known from the prior art may be prone to disruption of local perfusion.

It will be appreciated that anastomosis and/or coupling or sealing may be carried out at different anatomical locations in the body. In the gastrointestinal (GI) tract the esophagus, stomach, small bowel and large bowel may be subject to anastomosis or coupling procedures. It will be appreciated that many resections of gastrointestinal organs are followed by sealing procedures or anastomoses to restore continuity especially anastomosis between esophagus and stomach, stomach and small bowel, small bowel and small bowel, small bowel and colon, colon and colon, and colon and rectum.

It will be appreciated that it may be envisaged that a suitable plurality of couplers are affixed to the tissues at the same time. Alternatively, the device according to the invention may be arranged for allowing only a sequential insertion and affixing of the couplers. Those skilled in the art would readily appreciate that for these situations different loading units may be required. Preferably, the loading units may be synchronized for enabling simultaneous discharge of the first body of the coupler into the tissues. Such synchronization may be enabled using a suitable mechanical drive.

These and other aspects of the invention will be discussed with reference to drawings wherein like reference signs correspond to like elements. It will be appreciated that the drawings are presented for illustrative purposes only and may not be used for limiting the scope of the appended claims.

DETAILED DESCRIPTION OF THE DRAWINGS

WO83/00614, which is incorporated by reference in its entirety in the present patent application, shows (see FIG. 9) and describes a first prior art stapler apparatus, the apparatus including a first working element (staple holding assembly 150) that is displaceably arranged with respect to a second working element (anvil 130) so that at least a first relative stand (i.e. first relative position) and a second relative stand (i.e. second relative position) between the first working element (150) and a second working element (130) is provided. In the first relative stand, a coupling space is provided between the first working element (150) and the second working element (130), for receiving a first tissue portion and a second tissue portion for coupling. In the second stand, the first working element cooperates with the second working element for depositing a plurality of U-shaped surgical staples. In FIGS. 9-12 of WO83/00614, the staples are oriented in so that the longitudinal axis of the base of each staple is radial with respect to the staple holding assembly. The device is configured to firmly press all staples together, to fix the tissue portions tightly to each other, with a relatively large stapling force (to seal a gap between the tissue portions preventing leakage).

Figure 1A:
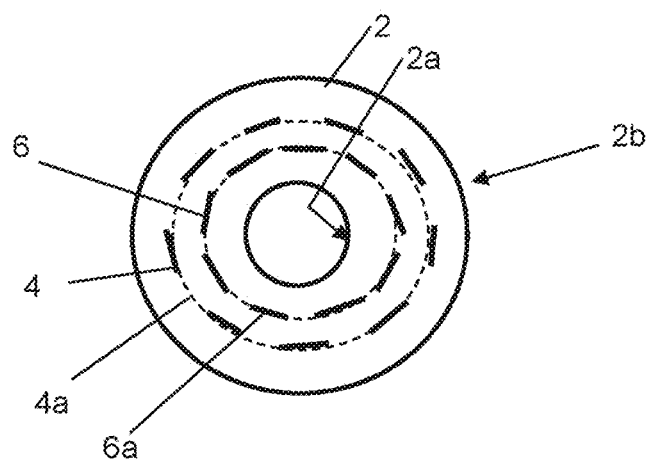
FIG. 1a presents a schematic embodiment of a conventional circular stapling technique, representing the orientation of the staples.
Figure 1B:
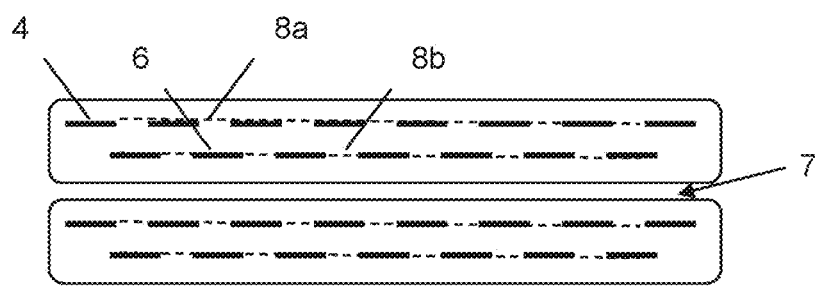
FIG. 1b presents a schematic embodiment of a conventional linear stapling technique, representing the orientation of the staples.

FIGS. 1a, 1b of the present patent application presents schematic embodiments of another conventional, gastrointestinal inverting stapling techniques, according to the prior art. Particularly, FIG. 1a shows the configuration of staples in the first working element, in transversal cross-section A substantially circular cut-line of an intestine is indicated at 2a. During coupling, two substantially ring-shaped intestine sections are positioned between the first working element and the second working element, positioned onto each other during connection, and connected by couplers 4, 6. In this case, stapling lines, as usually used in intestinal stapling devices whether circular (FIG. 1a) comprising two rows 4a, 6a or linear (FIG. 1b) 8a, 8b of interdigitating and overlapping staples 4, 6, particularly surrounding the cut-line 2a of the tissue 2. The staples 4, 6 (particularly their bases) are arranged along substantially concentric circles 6a, 4a. FIG. 1b shows another example of a conventional linear stapling technique, wherein two linear arrays of staples 4, 6 extend (with their bases) along linear staple lines 8a, 8b, in parallel with a linear cut-end 7. Although these configurations may lead to a water-tight closure, they have several disadvantages. U-shaped staples which are used for pinching the tissue 2 and are pushed against an aforementioned anvil (not shown) on the second working element for causing the ends of the staple to bend inwardly thereby compressing the tissue. Moreover, the concentric or linear interdigitated orientation of the staplers parallel to the cutting plane may be prone to disruption of local perfusion, especially in the presence of post-surgical edema.

It is found that when postoperative edema is developing, or when the staple force applied to the affixed tissue portions is too high the staple bodies 4, 6 may substantially obstruct blood flow to the anastomotic area and the cut end 2a. This may disadvantageously lead to ischemia and tissue necrosis, even more so when the respective rows of the staples are provided in such a way that a spacing between respective staples in one ring spatially corresponds to a body of a staple in the adjacent row.

Figure 2A:
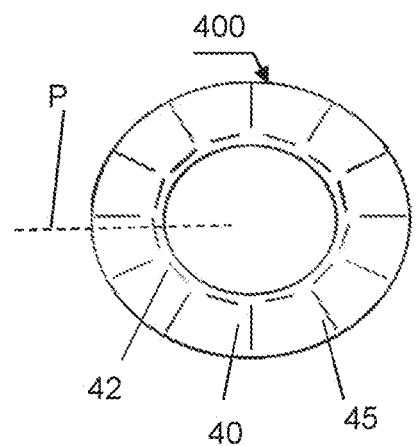
FIG. 2a presents in a schematic way, in a front view, an embodiment of a working element of the surgical device according to an aspect of the invention, particularly of a circular stapling apparatus.

FIG. 2a presents a schematic embodiment, in front view (i.e. towards a coupler holding/containing surface 40), of a working element 400 according to an aspect of the invention, particularly for a circular coupling (e.g. stapling) apparatus. The working element can be similar to the staple holding assembly (150) shown in FIG. 9 of WO83/00614. In the working element 400 according to the present aspect, a surface 40 is provided wherefrom the suitable plurality of couplers (e.g. staples) may be supplied. In this case, the working element 400 comprises a set of circularly arranged first couplers (in this case staples 42), extending along a substantially circular inner line (sealing line), as well as a set of differently oriented, second, couplers. The second couplers are separate/spaced-apart from the first couplers, in this example. Also in this example, the second couplers are an array of substantially radially arranged, spaced-apart, couplers (in this case staplers 45), viewed in front view. More particularly, the orientation of each second coupler is such that it lies in/defines a respective virtual coupler plane P (one being depicted with a dashed line in FIG. 2a) that intersects the substantially circular inner line—i.e. sealing line—that is defined by the arrangement of the first couplers 42. It should be observed that in the present drawing, the bases of staples 42, 45 are shown. The skilled person will appreciate that each staple 42, 45 as such also includes two opposite clamping legs, extending substantially normally with respect to the respective base. Accordingly, in use, the inner (proximal) row of the couplers 42 can be provided adjacent to a cutting end of a tubular tissue (see FIG. 1a), such as an intestine 2. The outer (distal) row of the radial couplers 45 can be provided in the tissues in a substantially radial orientation with respect to the cutting end. As has been explained with reference to the foregoing the inner ring of circular positioned couplers 42 is advantageously provided near the cut-end 2a of the tubular structure, which ensures hemostasis and watertight sealing (along an aforementioned inner sealing line), preventing leakage of contents of the lumen. The outer substantially radial couplers 45 ensure maximal perfusion at the anastomotic site, the anastomotic healing line.

It should be observed that the sealing line staples are nearly directly adjacent and the healing line staples are more widely apart.

It should also be observed that the staples of the healing line are positioned interdigitating and not overlapping with the staples of the sealing line, keeping maximally away from the high pressures zones inflicted by the sealing line.

It should be observed that in the example of FIG. 2a, each virtual plane P, defined by the orientation of a respective second coupler, intersects the substantially circular inner line substantially normally. However, that is not required. The second couplers 45 can also have different orientations, for example such that the virtual plane P intersects the circular inner line at an angle smaller or larger than 90° (viewed in the front view), for example an angle in the range of 30 to 89 degrees.

Figure 2B:
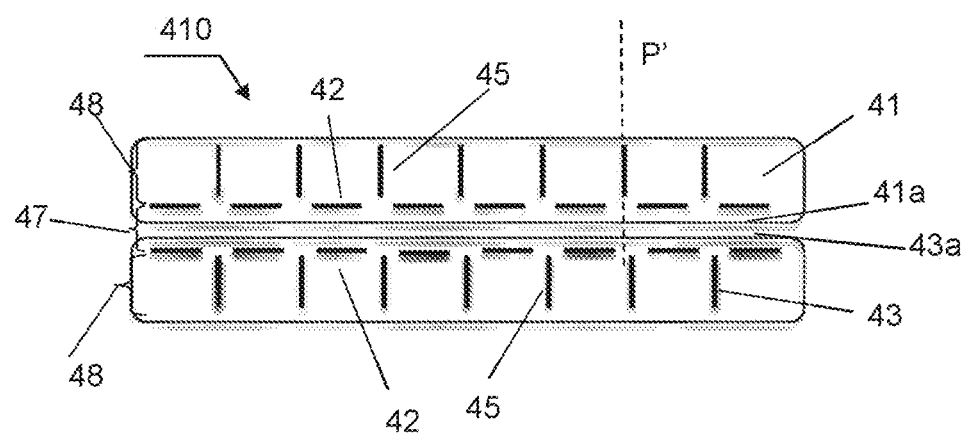
FIG. 2b presents in a schematic way, in a front view, an embodiment of a working element of the surgical device according to an aspect of the invention, particularly of a linear stapling apparatus.

FIG. 2b presents in a schematic way an embodiment of a working element 410, according to an aspect of the invention, for linear stapling. The coupling region is schematically divided into an the cut-end 47, where the tissue is divided in two parts, and an outer coupling region 48, where a double layer of tissue (i.e. two tissue parts) is coupled. The surfaces 41a, 43a correspond to the cut end. In accordance with the aspect of the invention, a parallel or concentric row of couplers 42 is provided close to the cut ends 41a, 43a, for providing a tissue sealing line. Further, a second set of spaced-apart couplers 45 is provided which are positioned, in this example in a substantially normal orientation with respect to the cutting ends 41a, 43a (i.e. the sealing line). Particularly, in this example, the orientation of each second coupler 45 is such that it lies in a respective virtual plane P' (one being depicted with a dashed line in FIG. 2b) that intersects the substantially linear sealing line defined by the linear arrangement of the first couplers 42, for example normally (as in the drawing), or for example at an angle smaller or larger than 90° (viewed in the front view), for example an angle in the range of 30 to 89 degrees.

According to a preferred embodiment, the first working element and the second working element are configured to deposit each first coupler into the coupling space with a relatively high pressure, to allow a proper sealing of the tissue along the sealing line (the sealing particularly involving locally blocking blood flood, along the sealing line). Then, very good results can be achieved in case the working elements deposit each second coupler into the coupling space (and remote from the first couplers) at a relatively low pressure, the low pressure being lower than the high pressure. For example, the working elements can bring the second couplers into respective tissue holding or clamping positions, using the relatively low pressure, such that the second couplers can hold the two tissue parts locally together, without locally obstructing blood flow.

Figure 3A:
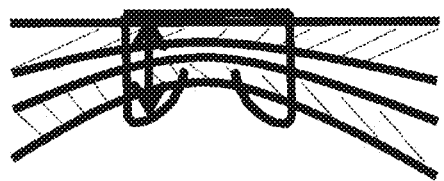
FIG. 3a presents in a schematic way, in a front view, an embodiment of a staple that is compressed in a conventional way, comprising the affixed tissue with high pressure.

FIG. 3a presents a schematic embodiment of a bent staple with relatively high pressure in the comprised tissue, according to conventional staple bending. The red arrow shows a short height from the base of the staple to the curve of the bent leg. Tissues that are held by this staple are compressed, leading to relatively high pressure.

Figure 3B:
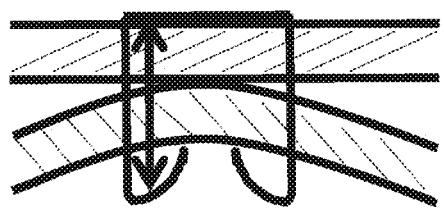
FIG. 3b presents in a schematic way in a front view, an embodiment of a staple that is compressed according to an aspect of the invention with proper apposition of the tissues, without high pressure, securing proper circulation.

FIG. 3b presents a schematic embodiment of a bent staple with relatively low pressure in the comprised tissue, according to staple bending according to this invention. Legs of the staple can be longer like in this figure, but not necessarily. Also the legs of the staple can be less bent, but not necessarily. The red arrow shows more height from the base of the staple to the curve of the bent leg. Tissues that are held by this staple are less compressed, leading to relatively low pressure.

Figure 4A:
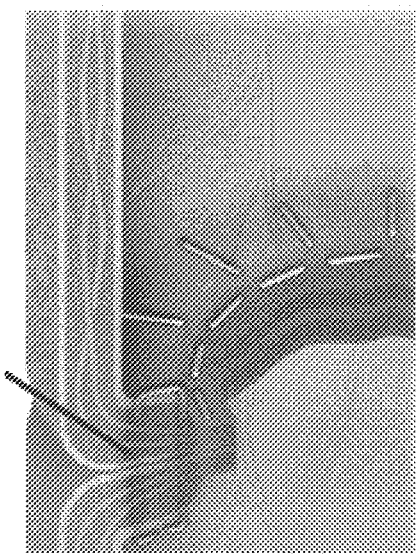
FIG. 4a presents in a schematic way the effect of the orientation and compression of staple configuration of invention on perfusion of the tissues to be coupled.

FIG. 4a presents a schematic cross section of a tubular intestine, in which the effect of the invention is shown: longitudinally oriented blood vessels can traverse between the radially oriented staples of the healing line, with wide interspaces, with adjusted height of the compressed staple, preventing compression of aforementioned blood vessels, and so presenting optimal perfusion and optimal healing conditions to the tissues in this healing line. The inner staple line compresses and obstructs the blood vessels to form a sealing line.

Figure 4B:
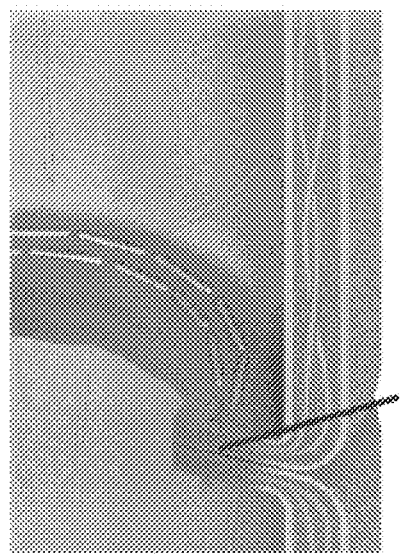
FIG. 4b presents in a schematic way the effect of the orientation and compression fo staple configuration on perfusion of conventional coupling/stapling on the tissues to be coupled.

FIG. 4b presents a schematic cross section of a tubular intestine, in which the effect of conventional stapling is shown: the highly compressed, transverse overlapping staple lines obstruct the bloodflow completely in the region to be coupled, thereby inducing necrosis and possibly leakage.

Figure 5A:
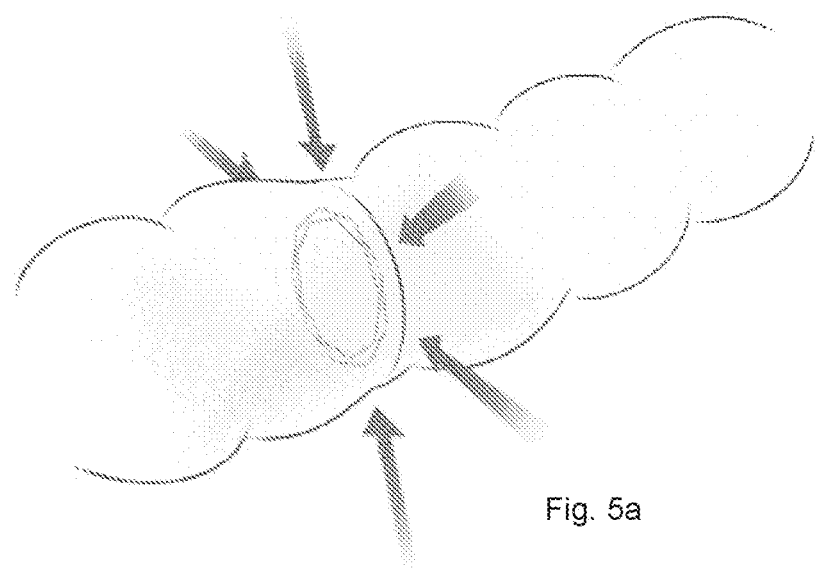
FIG. 5a presents in a schematic way the lack of radial distension that is permitted by the double concentric overlapping staple rows of the conventional stapler

FIG. 5a presents a schematic representation of a bowel showing the lack of distension possibilities of a conventional double, overlapping staple line with concentric staples. When voluminous content passes the coupled region, the staple lines prevent radial stretching and obstruct passage, possibly leading to functional problems.

Figure 5B:
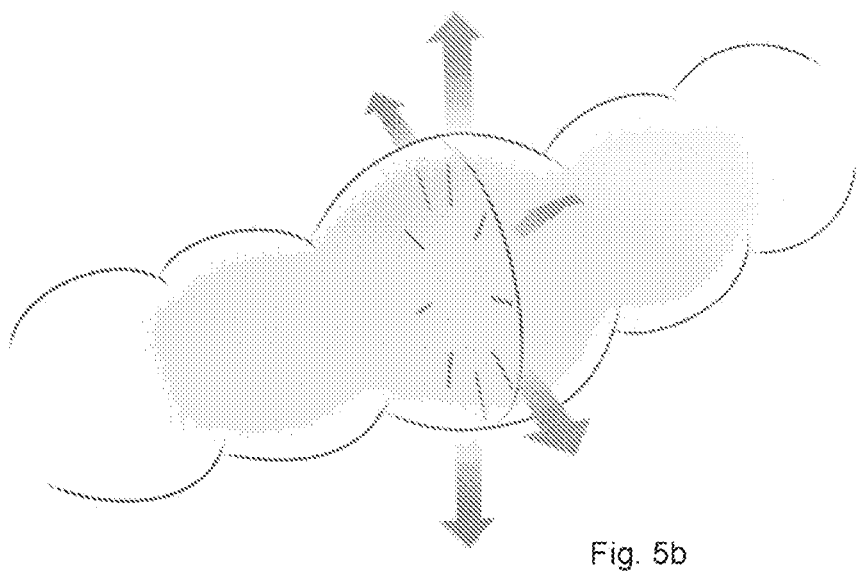
FIG. 5b presents in a schematic way the capacity to distend radially when voluminous intestinal content is passing, due to radial orientation of the stapler of the invention, following shedding of the sealing line

FIG. 5b presents a schematic representation of a bowel showing the distension potential of the invention, due to radial orientation of the staples in the healing line, following shedding of the sealing line.

While specific embodiments have been described above, it will be appreciated that the invention may be practiced otherwise than as described. Moreover, specific items discussed with reference to any of the isolated drawings may freely be inter-changed supplementing each other in any particular way. The descriptions above are intended to be illustrative, not limiting. Thus, it will be apparent to one skilled in the art that modifications may be made to the invention as described in the foregoing without departing from the scope of the claims set out below.

For instance, there can be provided a plurality of first couplers, defining a sealing line. Alternatively, there can be provided a single first coupler to define the sealing line, for example a single ring shaped first coupler to provide a closed-loop sealing line or a single linear first coupler to provide a linear sealing line.

The invention claimed is:

1. A surgical device for enabling gastro-intestinal anastomosis using tissue couplers, the device comprising a first working element and a second working element, the first working element being displaceably arranged with respect to the second working element so that at least a first relative stand and a second relative stand between the first working element and a second working element are provided,
wherein in the first relative stand a coupling space is provided between the first working element and the second working element, for receiving a first tissue portion and a second tissue portion for coupling, wherein in the second stand the first working element is adapted to cooperate with the second working element for depositing staples or couplers in said coupling space, for achieving said coupling along a coupling region,
wherein the first working element and/or the second working element comprise first staples or couplers and second staples or couplers, wherein the first staples or couplers are aligned parallel to a cut line of the tissues to define a tissue sealing line,
wherein the second staples or couplers each define a respective virtual plane (P; P') that intersects the tissue sealing line in an intersection point, wherein the virtual planes have an orientation that is normal with respect to an orientation of the said tissue sealing line in the intersection point, to define a tissue healing line, and
wherein a first distance between two adjacent first staples or couplers is smaller than a second distance between two adjacent second staples or couplers, when projected onto the tissue sealing line, and wherein the second staples or couplers interdigitate and not overlap with the first staples or couplers.

2. The device according to claim 1, wherein there is a difference in pressure in the comprised tissue in the sealing line as compared to pressure in the comprised tissue in the healing line.

3. The device according to claim 2, wherein the pressure in the comprised tissue in the sealing line is substantially higher as compared to pressure in the comprised tissue in the healing line.

4. The device according to claim 3, wherein the difference in pressure in the comprised tissue is produced by alternating a height of the drivers pushing the staples of couplers of the first working element towards an anvil of the second working element, where the drivers of the sealing line are longer than the drivers of the healing line, the anvil being positioned and shaped identically for both the sealing line and the healing line, resulting in less compressed staples or couplers in the healing line as compared to the staples or couplers in the sealing line, resulting in more inner space or room for the tissue within the closed staple or coupler in the healing line as compared to the inner space or room for the tissue within the closed staple or coupler in the sealing line.

5. The device according to claim 3, wherein the difference in pressure in the comprised tissue is produced or coproduced by alternating the depth of the receiving parts of the anvil of the second working element receiving the staples or couplers, where the depth of the anvil at the healing line is substantially deeper than the depth of the anvil at the sealing line, resulting in less compressed staples or couplers in the healing line as compared to the staples or couplers in the sealing line, resulting in more inner space or room for the tissue within the closed staple or coupler in the healing line as compared to the inner space or room for the tissue within the closed staple or coupler in the sealing line.

6. The device according claim 1, wherein the first working element and the second working element are configured to deposit each first coupler into the coupling space at a relatively high pressure, and to deposit each second coupler into the coupling space at a relatively low pressure, the low pressure being lower than the high pressure.

7. The device according to claim 1, where there is a difference in length between the legs of the first staples (sealing line) and the legs of the second staples (healing line), enabling a difference in height of a compressed staple, while still securing the tissue, the second staples of the healing line having longer legs than the first staples of the sealing line.

8. The device according to claim 7, wherein the configuration or regulator is arranged to limit the pressure to a value of about 25 mm Hg for the second couplers.

9. The device according to claim 1, further comprising a configuration or regulator for controlling pressure applied in use to the tissue for the second stand between the first working element and the second working element.

10. The device according to claim 1, wherein the distance between the base of the staple and the top of the bent leg of the second staple is at least 0.75 mm higher than the same distance in the first staple.

11. The device according to claim 1, wherein the tissue sealing line is linear, such that the second staples or couplers are normally oriented with respect to the first staples or couplers.

12. A surgical device for enabling gastro-intestinal anastomosis using one or more tissue couplers, for example a device according to any of the preceding claims, the device comprising a first working element and a second working element, the first working element being displaceably arranged with respect to the second working element so that at least a first relative stand and a second relative stand between the first working element and a second working element are provided, wherein in the first relative stand a coupling space is provided between the first working element and the second working element, for receiving a first tissue portion and a second tissue portion for coupling, wherein in the second stand the first working element cooperates with the second working element for depositing one or more couplers in the said coupling space, for achieving said coupling along a coupling region, wherein the first working element and/or the second working element contain one or more first couplers or staples and one or more second couplers or staples, wherein the one or more first couplers define a tissue sealing line and the one or more second couplers or staples define a tissue healing line, wherein the first working element and the second working element are configured to deposit each first coupler into the coupling space with a relatively high pressure, and to depositing each second coupler into the coupling space with a relatively low pressure, the low pressure being lower than the high pressure.

13. The device according to claim 1, wherein the tissue sealing line is linear, such that the second staples or couplers are normally oriented with respect to the first staples or couplers.

* * * * *